US012011427B2

(12) United States Patent
Tavazoie et al.

(10) Patent No.: US 12,011,427 B2
(45) Date of Patent: Jun. 18, 2024

(54) METHODS OF TREATING CANCER

(71) Applicant: Inspirna, Inc., New York, NY (US)

(72) Inventors: Masoud Fakhr Tavazoie, New York, NY (US); David M. Darst, Jr., New York, NY (US); Foster Casimir Gonsalves, Long Island City, NY (US); Isabel Kurth, New York, NY (US)

(73) Assignee: Inspirna, Inc., New York, NY (US)

( * ) Notice: Subject to any disclaimer, the term of this patent is extended or adjusted under 35 U.S.C. 154(b) by 0 days.

(21) Appl. No.: 17/119,661

(22) Filed: Dec. 11, 2020

(65) Prior Publication Data

US 2021/0177790 A1    Jun. 17, 2021

Related U.S. Application Data

(60) Provisional application No. 62/946,581, filed on Dec. 11, 2019.

(51) Int. Cl.
| | | |
|---|---|---|
| *A61K 31/195* | (2006.01) | |
| *A61K 9/00* | (2006.01) | |
| *A61K 31/4375* | (2006.01) | |
| *A61K 31/513* | (2006.01) | |
| *A61K 31/519* | (2006.01) | |
| *A61P 35/04* | (2006.01) | |

(52) U.S. Cl.
CPC .......... *A61K 31/195* (2013.01); *A61K 9/0019* (2013.01); *A61K 31/4375* (2013.01); *A61K 31/513* (2013.01); *A61K 31/519* (2013.01); *A61P 35/04* (2018.01)

(58) Field of Classification Search
CPC ................ A61K 31/195; A61K 9/0019; A61K 31/4375; A61K 31/513; A61K 31/519; A61P 35/04
See application file for complete search history.

(56) References Cited

U.S. PATENT DOCUMENTS

| | | |
|---|---|---|
| 3,870,709 A | 3/1975 | Hamanaka |
| 3,933,797 A | 1/1976 | Hamanaka |
| 3,972,872 A | 8/1976 | Hamanaka |
| 5,321,030 A | 6/1994 | Kaddurah-Daouk et al. |
| 5,324,731 A | 6/1994 | Kaddurah-Daouk et al. |
| 5,576,316 A | 11/1996 | Cohn |
| 5,750,193 A | 5/1998 | Nass et al. |
| 5,900,435 A | 5/1999 | Meglasson |
| 5,955,617 A | 9/1999 | Larsen et al. |
| 5,994,577 A | 11/1999 | Larsen et al. |
| 5,998,457 A | 12/1999 | Kaddurah-Daouk |
| 6,166,080 A | 12/2000 | Larsen et al. |
| 6,177,453 B1 | 1/2001 | Larsen et al. |
| 6,184,216 B1 | 2/2001 | Larsen et al. |
| 6,242,491 B1 | 6/2001 | Kaddurah-Daouk |
| 6,274,580 B1 | 8/2001 | Larsen et al. |
| 6,329,403 B1 | 12/2001 | Odaka et al. |
| 6,329,545 B1 | 12/2001 | Larsen et al. |
| 6,348,200 B1 | 2/2002 | Nakajima et al. |
| 6,518,299 B1 | 2/2003 | Chand et al. |
| 6,605,115 B1 | 8/2003 | Cooke et al. |
| 7,186,754 B2 | 3/2007 | Kaddurah-Daouk |
| 7,273,846 B2 | 9/2007 | Bednarek |
| 8,101,661 B2 | 1/2012 | Mickle |
| 8,118,884 B2 | 2/2012 | Ascione et al. |
| 8,685,916 B2 | 4/2014 | Jenkins et al. |
| 8,748,567 B2 | 6/2014 | Narasimhaswamy et al. |
| 8,765,115 B2 | 7/2014 | Fujiwara et al. |
| 8,927,500 B2 | 1/2015 | Guerlavais et al. |
| 8,937,090 B2 | 1/2015 | Kaminuma et al. |
| 9,040,497 B2 | 5/2015 | Tavazoie et al. |
| 9,492,414 B2 | 11/2016 | Tavazoie et al. |
| 9,827,217 B2 | 11/2017 | Martinez et al. |
| 9,884,813 B1 * | 2/2018 | Martinez .............. A61K 9/0019 |
| 2002/0049253 A1 | 4/2002 | Kaddurah-Daouk |
| 2002/0082448 A1 | 6/2002 | Larsen et al. |
| 2002/0086885 A1 | 7/2002 | Odaka et al. |
| 2004/0074504 A1 | 4/2004 | Cooke et al. |
| 2004/0126366 A1 | 7/2004 | Kaddurah-Daouk et al. |
| 2005/0020492 A1 | 1/2005 | Bednarek |
| 2005/0186158 A1 | 8/2005 | Kaddurah-Daouk |
| 2005/0186194 A1 | 8/2005 | Kaddurah-Daouk |
| 2005/0186195 A1 | 8/2005 | Kaddurah-Daouk |
| 2005/0226840 A1 | 10/2005 | Kaddurah-Daouk |
| 2005/0227996 A1 | 10/2005 | Kaddurah-Daouk |
| 2006/0159719 A1 | 7/2006 | Cooke et al. |
| 2006/0167402 A1 | 7/2006 | Cooke et al. |
| 2006/0241021 A1 | 10/2006 | Kaddurah-Daouk et al. |

(Continued)

FOREIGN PATENT DOCUMENTS

| | | |
|---|---|---|
| CA | 1016538 A | 8/1977 |
| CA | 2202265 A1 | 5/1996 |

(Continued)

OTHER PUBLICATIONS

Keane, Folfiri Therapy—14 day, NCCP Chemotherapy Regimen, Oct. 1, 2015 (Year: 2015).*
FDA, Camptosar (Irinotecan) Injection, intravenous infusion, Dec. 2014 (Year: 2014).*
American Cancer Society, What is Cancer Recurrence?, American Cancer Society, Feb. 12, 2016 (Year: 2016).*
"Nonlinear pharmacokinetics", Applied Biopharmaceutics & Pharmacokinetics, 6e Eds. Leon Shargel, et al. McGraw Hill, 2012 (Year: 2012).*
International Search Report and Written Opinion for International Patent Application No. PCT/US2016/048643, dated Oct. 25, 2016 (14 pages).
International Preliminary Report on Patentability for International Application No. PCT/US2016/048643, dated Feb. 27, 2018 (6 pages).

(Continued)

*Primary Examiner* — John S Kenyon
*Assistant Examiner* — Gillian A Hutter
(74) *Attorney, Agent, or Firm* — Clark & Elbing LLP

(57) ABSTRACT

The invention features methods of treating cancer with β-GPA. The disclosure also provides methods of treating cancer including combinations of β-GPA and additional anti-cancer therapies.

21 Claims, No Drawings

(56) References Cited

U.S. PATENT DOCUMENTS

| | | |
|---|---|---|
| 2007/0027090 A1 | 2/2007 | Kaddurah-Daouk et al. |
| 2007/0253944 A1 | 11/2007 | Kaddurah-Daouk |
| 2009/0221706 A1 | 9/2009 | Kaddurah-Daouk et al. |
| 2010/0113353 A1 | 5/2010 | Cooke et al. |
| 2010/0179106 A1 | 7/2010 | Khan |
| 2010/0226870 A1 | 9/2010 | Kaddurah-Daouk |
| 2010/0233084 A1 | 9/2010 | Narasimhaswamy et al. |
| 2010/0292336 A1 | 11/2010 | Mickle |
| 2010/0292337 A1 | 11/2010 | Mickle |
| 2010/0329997 A1 | 12/2010 | Kaddurah-Daouk |
| 2011/0008272 A1 | 1/2011 | Kaddurah-Daouk |
| 2011/0021632 A1 | 1/2011 | Kaddurah-Daouk |
| 2011/0085993 A1 | 4/2011 | Kaddurah-Daouk |
| 2011/0111066 A1 | 5/2011 | Ferguson et al. |
| 2011/0158925 A1 | 6/2011 | Ascione et al. |
| 2011/0262355 A1 | 10/2011 | Jenkins et al. |
| 2011/0262359 A1 | 10/2011 | Jenkins et al. |
| 2012/0141391 A1 | 6/2012 | Kaddurah-Daouk |
| 2012/0232066 A1 | 9/2012 | Jenkins et al. |
| 2012/0232111 A1 | 9/2012 | Kaminuma et al. |
| 2012/0245211 A1 | 9/2012 | Clark et al. |
| 2012/0258925 A1 | 10/2012 | Aggen et al. |
| 2012/0295834 A1 | 11/2012 | Jenkins et al. |
| 2012/0328561 A1 | 12/2012 | Fujiwara et al. |
| 2013/0011364 A1 | 1/2013 | Fichert et al. |
| 2013/0021085 A1 | 1/2013 | Kumar et al. |
| 2013/0040877 A1 | 2/2013 | Kofoed et al. |
| 2013/0058958 A1 | 3/2013 | Bowen et al. |
| 2013/0059914 A1 | 3/2013 | Jenkins et al. |
| 2013/0072462 A1 | 3/2013 | Khan |
| 2013/0090488 A1 | 4/2013 | Dietz |
| 2013/0123169 A1 | 5/2013 | Kawahata et al. |
| 2013/0210701 A1 | 8/2013 | Jenkins et al. |
| 2013/0210745 A1 | 8/2013 | Guerlavais et al. |
| 2013/0274205 A1 | 10/2013 | Guerlavais et al. |
| 2013/0281324 A1 | 10/2013 | Gouliaev et al. |
| 2013/0281410 A1 | 10/2013 | Renshaw |
| 2014/0045798 A1 | 2/2014 | Khan |
| 2014/0121152 A1 | 5/2014 | Jenkins et al. |
| 2014/0141069 A1 | 5/2014 | Brewster |
| 2014/0206597 A1 | 7/2014 | Jenkins et al. |
| 2014/0224737 A1 | 8/2014 | Fichert et al. |
| 2014/0294727 A1 | 10/2014 | Narasimhaswamy et al. |
| 2014/0378534 A1 | 12/2014 | Tavazoie et al. |
| 2015/0051155 A1 | 2/2015 | Guerlavais et al. |
| 2015/0126520 A1 | 5/2015 | Chiodo et al. |
| 2017/0056352 A1 | 3/2017 | Martinez et al. |
| 2017/0056353 A1 | 3/2017 | Martinez et al. |

FOREIGN PATENT DOCUMENTS

| | | |
|---|---|---|
| CA | 2329004 A1 | 1/2000 |
| CA | 2376375 A1 | 12/2000 |
| CA | 2376943 A1 | 1/2001 |
| CA | 2473229 A1 | 7/2003 |
| CA | 2698755 A1 | 3/2009 |
| CA | 2795222 A1 | 10/2011 |
| CA | 2801624 A1 | 12/2011 |
| CA | 2827662 A1 | 9/2012 |
| CA | 2852468 A1 | 4/2013 |
| CA | 2862038 A1 | 8/2013 |
| CA | 2864120 A1 | 8/2013 |
| CN | 102850242 A | 1/2013 |
| CN | 103288685 A | 9/2013 |
| CN | 104341450 A | 2/2015 |
| EP | 0260118 A1 | 3/1988 |
| EP | 0426100 A1 | 5/1991 |
| EP | 0793646 A1 | 9/1997 |
| EP | 1093370 A1 | 4/2001 |
| EP | 1189623 A2 | 3/2002 |
| EP | 1656945 A1 | 5/2006 |
| EP | 1746099 A1 | 1/2007 |
| EP | 1880711 A1 | 1/2008 |
| EP | 2397127 A1 | 12/2011 |
| EP | 2399885 A1 | 12/2011 |
| EP | 2567705 A2 | 3/2013 |
| FR | 2181713 A1 | 12/1973 |
| GB | 1379502 A | 1/1975 |
| JP | 2579323 B2 | 2/1997 |
| JP | 2004-537581 A | 12/2004 |
| JP | 2005-518346 A | 6/2005 |
| JP | 2005-527491 A | 9/2005 |
| JP | 3745439 B2 | 2/2006 |
| JP | 2009-503003 A | 1/2009 |
| JP | 4317599 B2 | 8/2009 |
| JP | 2010-521420 A | 6/2010 |
| JP | 2010-143922 A | 7/2010 |
| JP | 2010-143928 A | 7/2010 |
| JP | 2010-260861 A | 11/2010 |
| JP | 2012-012409 A | 1/2012 |
| JP | 2012-512855 A | 6/2012 |
| JP | 2013-516414 A | 5/2013 |
| JP | 2013-525348 A | 6/2013 |
| JP | 2013-534903 A | 9/2013 |
| JP | 5284088 B2 | 9/2013 |
| JP | 2013-538106 A | 10/2013 |
| JP | 2014-518546 A | 7/2014 |
| JP | 5544024 B2 | 7/2014 |
| JP | 2014-521656 A | 8/2014 |
| JP | 2014-159462 A | 9/2014 |
| JP | 2015-500262 A | 1/2015 |
| WO | WO-1990/009192 A1 | 8/1990 |
| WO | WO-1992/008456 A2 | 5/1992 |
| WO | WO-1994/016687 A1 | 8/1994 |
| WO | WO-95/19769 A1 | 7/1995 |
| WO | WO-1996/016031 A1 | 5/1996 |
| WO | WO-1997/013507 A1 | 4/1997 |
| WO | WO-1997/014401 A1 | 4/1997 |
| WO | WO-1997/044324 A1 | 11/1997 |
| WO | WO-2000/000195 A1 | 1/2000 |
| WO | WO-2000/074701 A2 | 12/2000 |
| WO | WO-2001/000203 A1 | 1/2001 |
| WO | WO-2003/013574 A1 | 2/2003 |
| WO | WO-2003/039449 A2 | 5/2003 |
| WO | WO-2003/060091 A2 | 7/2003 |
| WO | WO-2003/101402 A2 | 12/2003 |
| WO | WO-2004/069232 A2 | 8/2004 |
| WO | WO-2007/014756 A1 | 2/2007 |
| WO | WO-2008/043024 A2 | 4/2008 |
| WO | WO-2008/054544 A2 | 5/2008 |
| WO | WO-2008/092591 A2 | 8/2008 |
| WO | WO-2009/033130 A1 | 3/2009 |
| WO | WO-2009/098142 A1 | 8/2009 |
| WO | WO-2010/070243 A1 | 6/2010 |
| WO | WO-2011/082076 A1 | 7/2011 |
| WO | WO-2011/121008 A1 | 10/2011 |
| WO | WO-2011/127933 A1 | 10/2011 |
| WO | WO-2011/133149 A1 | 10/2011 |
| WO | WO-2011/133150 A1 | 10/2011 |
| WO | WO-2011/133348 A1 | 10/2011 |
| WO | WO-2011/139718 A1 | 11/2011 |
| WO | WO-2011/143534 A1 | 11/2011 |
| WO | WO-2011/160857 A2 | 12/2011 |
| WO | WO-2012/024611 A1 | 2/2012 |
| WO | WO-2012/047630 A2 | 4/2012 |
| WO | WO-2012/122412 A2 | 9/2012 |
| WO | WO-2012/122420 A2 | 9/2012 |
| WO | WO-2012/122422 A2 | 9/2012 |
| WO | WO-2012/138214 A1 | 10/2012 |
| WO | WO-2012/173846 A2 | 12/2012 |
| WO | WO-2013/016668 A2 | 1/2013 |
| WO | WO-2013/059525 A1 | 4/2013 |
| WO | WO-2013/083642 A1 | 6/2013 |
| WO | WO-2013/123266 A1 | 8/2013 |
| WO | WO-2013/123267 A1 | 8/2013 |
| WO | WO-2013/183055 A1 | 12/2013 |
| WO | WO-2014/071067 A2 | 5/2014 |
| WO | WO-2014/072490 A1 | 5/2014 |
| WO | WO-2014071067 A2 * | 5/2014 | ........... A61K 31/197 |
| WO | WO-2014/138492 A1 | 9/2014 |
| WO | WO-2016/168857 A1 | 10/2016 |

(56) References Cited

FOREIGN PATENT DOCUMENTS

| WO | WO-2016/176636 A1 | 11/2016 |
| WO | WO-2017/035331 A1 | 3/2017 |

OTHER PUBLICATIONS

International Search Report and Written Opinion for International Application No. PCT/US17/20266, dated May 22, 2017 (13 pages).
Ohira et al., "Effects of creatine and beta-guanidinopropionic acid on the growth of Ehrlich ascites tumor cells: i.p. injection and culture study," Biochim Biophys Acta. 1243(3):367-72 (1995).
Extended European Search Report for European Application No. 16840104.0, dated Mar. 1, 2019 (8 pages).
Dietrich et al., "Carbon-13 Nuclear Magnetic Resonance Studies of Creatine, Creatinine and some of their Analogs," Org Magnet Res. 13(2):79-88 (1980).
Rodionow et al., Zhurnal Obshchei Khimi; 18:2023-2032 (1948).
Holm et al., "Mitteilungen aus dem pharmazeutisch-chemischen Institut der Universität Marburg," Archiv De Pharmazie. 242:590-612 (1904).
Loo et al., "Extracellular metabolic energetics can promote cancer progression," Cell 160(3):393-406 (2015).
International Preliminary Report on Patentability for International Application No. PCT/US2017/020266, dated Sep. 3, 2019 (7 pages).
Compound (CAS RN 1348115-72-9), entering STN Chemical database and accessible to public on Dec. 4, 2011.
Dodd et al., "Selective Amino Acid Substitutions Convert the Creatine Transporter to a gamma-Aminobutyric Acid Transporter," J Biol Chem. 282(21):15528-33 (2007).
Dodd et al., "Substituted cysteine accessibility of the third transmembrane domain of the creatine transporter: defining a transport pathway," J Biol Chem. 280(38):32649-54 (2005).
Extended European Search Report for European Patent Application No. 15786453.9, dated Dec. 6, 2017 (11 pages).
Fitch et al., "Inhibition of Creatine and Phosphocreatine Accumulation in Skeletal Muscle and Heart," Metabolism. 29(7):686-90 (1980).
International Preliminary Report on Patentability for International Application Patent No. PCT/US2015/028633, dated Nov. 1, 2016 (5 pages).
International Search Report and Written Opinion for International Application No. PCT/US15/28633, dated Aug. 4, 2015 (11 pages).
Juaristi et al., "Enantioselective synthesis of beta-amino acids. 4. 1,2 asymmetric induction in the alkylation of 1-Benzoyl-3,6(S)-dimethylperhydropyrimidin-4-one. Preparation of the like and unlike stereoisomers of 2-Methyl- and 2-Benzyl-3(S)-aminobutanoic acid," J Org Chem. 58(8):2282-5 (1993).
Kalinoski et al., "Specific L-arginine taste receptor sites in the catfish, *Ictalurus punctatus*: biochemical and neurophysiological characterization," Brain Res. 488(1-2):163-73 (1989).
Lal et al., "A practical synthesis of free and protected guanidino acids from amino acids," Tetrahedron Lett. 37(14):2483-6 (1996).
Larsen et al., "Synthesis and Biological Activity of Analogues of the Antidiabetic/Antiobesity Agent 3-guanidinopropionic Acid: Discovery of a Novel Aminoguanidinoacetic Acid Antidiabetic Agent," J Med Chem. 44(8):1217-30 (2001).
Marenich et al., "Quantitative antidiabetic activity prediction for the class of guanidino- and aminoguanidinopropionic acid analogs based on electron-conformational studies," J Chem Inf Model. 48(3):556-68 (2008).
Martin et al., "Specific targeting of tumor cells by the creatine analog cyclocreatine," Int J Oncol. 9(5):993-9 (1996).
McLaughlin et al., "Specificity of creatine kinase for guanidino substrates. Kinetic and Proton nuclear magnetic relaxation rate studies," J Biol Chem. 247(13):4382-8 (1972).
Meffert et al., "Elevated creatine kinase activity in primary hepatocellular carcinoma," BMC Gastroenterol. 5:9 (2005) (7 pages).
Rendina et al., "The design and synthesis of inhibitors of dethiobiotin synthetase as potential herbicides," Pestic Sci. 55(3):236-47 (1999).
Vaillancourt et al., "Synthesis and Biological Activity of Aminoguanidine and Diaminoguanidine Analogues of the Antidiabetic/Antiobesity Agent 3-Guanidinopropionic Acid," J Med Chem. 44(8):1231-48 (2001).
Schafer et al., "Failure is an option: learning from unsuccessful proof-of-concept trials," Drug Discov Today. 13(21-22):913-6 (2008).
Horig et al., "From bench to clinic and back: Perspective on the 1st IQPC Translational Research conference," J Trans Med. 2(1):44 (2004) (8 pages).
Van Cutsem et al., "Cetuximab and chemotherapy as initial treatment for metastatic colorectal cancer," N Engl J Med. 360(14):1408-17 (2009).
International Search Report and Written Opinion for International Application No. PCT/US20/64317, dated Mar. 22, 2021 (11 pages).
Karamat et al., "The acute effect of beta-guanidinopropionic acid versus creatine or placebo in healthy men (ABC Trial): study protocol for a randomized controlled trial," Trials. 16:56 (Feb. 2015) (10 Pages).
Karamat et al., "The acute effect of beta-guanidinopropionic acid versus creatine or placebo in healthy men (ABC-Trial): A randomized controlled first-in-human trial," Br J Clin Pharmacol. 83:2626-2635 (Dec. 2017).
Oudman et al., "The Effect of the Creatine Analogue Beta-guanidinopropionic Acid on Energy Metabolism: A Systematic Review," PLoS One. 8(1):e52879 (Jan. 2013) (13 Pages).
Del Fresno et al., "Combinatorial approaches towards the discovery of new tryptase inhibitors," Bioorg Med Chem Lett. 15(6):1659-64 (Mar. 15, 2005).
Extended European Search Report for European Application No. 20899002.8, dated Oct. 27, 2023 (8 pages).

\* cited by examiner

METHODS OF TREATING CANCER

BACKGROUND

β-Guanidinopropionic acid (β-GPA), also referred to as guanidinopropionic acid, beta-guanidinopropionic acid or, N-(aminoiminomethyl)-beta-alanine is a creatine analog. Studies on animals (rats, monkeys, hamsters) show that acidic guanidine derivatives such as β-GPA can ameliorate hyperglycemia in animal models of noninsulin-dependent diabetes. Accordingly, it is sometimes used as a dietary supplement in diabetic patients to regulate blood sugar levels. β-GPA has recently been found to be effective for the suppression of metastasis, particularly liver metastasis in gastrointestinal cancers, e.g., see International Patent Publication WO2014/071067. Accordingly, the development of dosing regimens of β-GPA which result in efficacy while reducing adverse events for the treatment of cancer are needed.

SUMMARY OF THE INVENTION

The invention features methods of treating cancer by administering about 1,500 mg to about 4,000 mg of β-GPA twice daily. The inventors have discovered that this dosing regimen surprisingly results in higher than expected levels of systemically circulating β-GPA.

Accordingly, in one aspect, the invention features a method of treating cancer (e.g., gastrointestinal cancer such as colon cancer or gastric cancer, pancreatic cancer, liver cancer, breast cancer, prostate cancer, lung cancer, adenocarcinoma of the esophagogastric junction, and melanoma) in a subject in need thereof. This method includes administering about 1,500 mg to about 4,000 mg (e.g., about 1,500 mg to about 2,000 mg, about 1,750 mg to about 2,250 mg, about 2,000 mg to about 2,500 mg, about 2,250 mg to about 2,750 mg, about 2,400 mg to about 2,800 mg, about 2,700 mg to about 3,000 mg, about 2,750 mg to about 3,250 mg, about 3,100 mg to about 3,400 mg, about 3,200 mg to about 3,600 mg) of β-GPA, or a pharmaceutically acceptable salt thereof to the subject twice per day. In some embodiments of any of the foregoing methods, the method includes administering between about 2,400 mg and about 3,600 mg of β-GPA, or a pharmaceutically acceptable salt thereof to the subject twice per day. In some embodiments of any of the foregoing methods, the method includes administering about 2,400 mg of β-GPA, or a pharmaceutically acceptable salt thereof to the subject twice per day. In some embodiments of any of the foregoing methods, the method includes administering about 3,600 mg of β-GPA, or a pharmaceutically acceptable salt thereof to the subject twice per day.

In some embodiments of any of the foregoing methods, the method further includes administering one or more further anti-cancer therapies (e.g., radiation therapy, surgery, and/or one or more therapeutic agents). In some embodiments of any of the foregoing methods, the one or more further anti-cancer therapies includes folinic acid, fluorouracil, irinotecan, and/or oxaliplatin. In some embodiments of any of the foregoing methods, the one or more further anti-cancer therapies includes FOLFIRI, i.e., folinic acid, fluorouracil, and irinotecan. In some embodiments of any of the foregoing methods, the method includes administering about 180 mg/m$^2$ of irinotecan intravenously over 90 minutes concurrently with about 400 mg/m$^2$ or 2×250 mg/m$^2$ folinic acid intravenously over 120 minutes followed by an optional about 400-500 mg/m$^2$ (e.g., about 400 mg/m$^2$) bolus of fluorouracil intravenously followed by an about 2400-3000 mg/m$^2$ (e.g., about 2400 mg/m$^2$) infusion of fluorouracil intravenously over 46 hours on days 1 and 15 of each 28-day cycle, e.g., repeated about every fourteen days. In some embodiments of any of the foregoing methods, the one or more therapeutic agents is cyclocreatine, a RNAi agent, a nucleic acid, a vector, 5-fluorouracil, oxaliplatin, irinotecan, capecitabine, gemcitabine, cetuximab, taxol, avastin, folinic acid (leucovorin), regorafenib, zaltrap, topoisomerase I inhibitors, etirinotecan pegol, tivantinib, sonolisib, sorafenib, linifanib, kinase inhibitors, telatinib, BMS-908662 (i.e., methyl N-[6-[2-(5-chloro-2-methylphenyl)-1-hydroxy-3-oxoisoindol-1-yl]-1H-benzimidazol-2-yl]carbamate), robatumumab, and/or IGF1-R inhibitors.

In some embodiments of any of the foregoing methods, the method further includes surgery (e.g., prior to, or subsequent to, administration of β-GPA, or a pharmaceutically acceptable salt thereof).

In some embodiments of any of the foregoing methods, the cancer is metastatic cancer (e.g., metastatic gastrointestinal cancer such as metastatic colon cancer or metastatic gastric cancer, metastatic pancreatic cancer, metastatic liver cancer, metastatic breast cancer, metastatic prostate cancer, metastatic lung cancer, metastatic adenocarcinoma of the esophagogastric junction, or metastatic melanoma).

In some embodiments of any of the foregoing methods, the cancer is gastrointestinal cancer (e.g., colorectal cancer, gastric cancer, or adenocarcinoma of the esophagogastric junction).

In some embodiments of any of the foregoing methods, the cancer expresses CKB. In some embodiments of any of the foregoing methods, the subject is identified to have, or to be at risk of having, metastatic cancer (e.g., on the basis of the expression level of CKB being above a predetermined reference value).

In some embodiments of any of the foregoing methods, the cancer is resistant to one or more therapeutic agents. In some embodiments of any of the foregoing methods, the cancer progressed on or after treatment with one or more anti-cancer therapies.

In some embodiments of any of the foregoing methods, the β-GPA, or a pharmaceutically acceptable salt thereof is the succinate salt of β-GPA (e.g., the 2:1 succinate salt of β-GPA).

Definitions

As used herein, the term "about" represents a value that is in the range of ±10% of the value that follows the term "about."

As used herein, the term "administration" refers to the administration of a composition (e.g., a compound or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal, and vitreal.

The term "cancer" refers to any cancer caused by the proliferation of malignant neoplastic cells, such as tumors, neoplasms, carcinomas, sarcomas, leukemias, and lymphomas.

A cancer "determined to be drug resistant," as used herein, refers to a cancer that is drug resistant, based on unresponsiveness or decreased responsiveness to a chemotherapeutic agent, or is predicted to be drug resistant based on a prognostic assay (e.g., a gene expression assay).

By a "drug resistant" cancer is meant a cancer that does not respond, or exhibits a decreased response to, one or more chemotherapeutic agents (e.g., any agent described herein).

As used herein, the term "failed to respond to a prior therapy" or "refractory to a prior therapy," refers to a cancer that progressed despite treatment with the therapy.

As used herein, "metastatic tumor" refers to a tumor or cancer in which the cancer cells forming the tumor have a high potential to or have begun to, metastasize, or spread from one location to another location or locations within a subject, via the lymphatic system or via hematogenous spread, for example, creating secondary tumors within the subject. Such metastatic behavior may be indicative of malignant tumors. In some cases, metastatic behavior may be associated with an increase in cell migration and/or invasion behavior of the tumor cells.

Examples of cancers that can be defined as metastatic include but are not limited to non-small cell lung cancer (e.g., non-squamous non-small cell lung cancer), breast cancer, ovarian cancer, colorectal cancer, biliary tract cancer, bladder cancer, brain cancer including glioblastomas and medulloblastomas, cervical cancer, choriocarcinoma, endometrial cancer, esophageal cancer, gastric cancer, hematological neoplasms, multiple myeloma, leukemia, intraepithelial neoplasms, liver cancer, lymphomas, neuroblastomas, oral cancer, pancreatic cancer, prostate cancer, sarcoma, skin cancer including melanoma, basocellular cancer, squamous cell cancer, testicular cancer, stromal tumors, germ cell tumors, thyroid cancer, and renal cancer.

As used herein, the term "pharmaceutical composition" refers to an active compound, formulated together with one or more pharmaceutically acceptable carriers. In some embodiments, active compound is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

A "pharmaceutically acceptable excipient," as used herein, refers any inactive ingredient (for example, a vehicle capable of suspending or dissolving the active compound) having the properties of being nontoxic and non-inflammatory in a subject. Typical excipients include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Those of ordinary skill in the art are familiar with a variety of agents and materials useful as excipients.

The term "pharmaceutically acceptable salt," as use herein, refers to those salts of the compounds described here that are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art.

The term "subject," as used herein, refers to a human or non-human animal (e.g., a mammal such as a non-human primate, horse, cow, or dog).

The term "treatment" (also "treat" or "treating"), in its broadest sense, refers to any administration of a substance (e.g., provided compositions) that partially or completely alleviates, ameliorates, relieves, inhibits, delays onset of, reduces severity of, and/or reduces incidence of one or more symptoms, features, and/or causes of a particular disease, disorder, and/or condition. In some embodiments, such treatment may be administered to a subject who does not exhibit signs of the relevant disease, disorder and/or condition and/or of a subject who exhibits only early signs of the disease, disorder, and/or condition. Alternatively, or additionally, in some embodiments, treatment may be administered to a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the description below. Other features, objects, and advantages of the invention will be apparent from the description and from the claims.

DETAILED DESCRIPTION OF THE INVENTION

The invention features methods of treating cancer by administering about 2,000 mg to about 4,000 mg of β-GPA twice daily. The inventors have discovered that this dosing regimen surprisingly results in higher than expected levels of circulating β-GPA.

β-GPA

β-GPA has the structure:

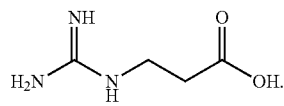

β-GPA is zwitterionic and highly soluble in water (>50 mg/mL), but has low solubility in organic solvents. β-GPA possesses a basic guanidino group, and is thus capable of forming both 1:1 (β-GPA:acid) and 2:1 (β-GPA:acid) salts with diacids. As used herein, a "2:1 salt" of β-GPA with a diacid, e.g., a 2:1 succinate salt, refers to a salt including two molecules of β-GPA and one molecule of the diacid, e.g., a "2:1 succinate salt" includes two molecules of β-GPA and one molecule of succinic acid.

Treatment Methods

β-GPA has recently been found to be effective for the suppression of metastasis. The mechanism of action has been hypothesized as inhibition of creatine transport and/or creatine kinase. The phosphocreatine system promotes metastasis by enhancing the survival of disseminated cancer cells in the liver by acting as an energetic store for ATP generation to endure hepatic hypoxia. Inhibition of creatine transport into cancer cells limits the amount of phosphocreatine available to use in the production of ATP. Inhibition of creatine kinase inhibits the production of ATP through conversion of phosphocreatine to creatine.

Typical vascularized tumors that can be treated with the methods of the invention include solid tumors, particularly carcinomas, which require a vascular component for the provision of oxygen and nutrients. Exemplary solid tumors include, but are not limited to, carcinomas of the lung, breast, bone, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, glioblastomas, neuroblastomas, Kaposi's sarcoma, and sarcomas.

Treating cancer can result in a reduction in size or volume of a tumor. For example, after treatment, tumor size is reduced by 5% or greater (e.g., 10%, 20%, 30%, 40%, 50%, 60%, 70%, 80%, 90% or greater) relative to its size prior to treatment. Size of a tumor may be measured by any reproducible means of measurement. For example, the size of a tumor may be measured as a diameter of the tumor.

Treating cancer may further result in a decrease in number of tumors. For example, after treatment, tumor number is reduced by 5% or greater (e.g., 10%, 20%, 30%, 40%, 50%, 60%, 70%, 80%, 90% or greater) relative to number prior to treatment. Number of tumors may be measured by any reproducible means of measurement, e.g., the number of tumors may be measured by counting tumors visible to the naked eye or at a specified magnification (e.g., 2×, 3×, 4×, 5×, 10×, or 50×).

Treating cancer can result in a decrease in number of metastatic nodules in other tissues or organs distant from the primary tumor site. For example, after treatment, the number of metastatic nodules is reduced by 5% or greater (e.g., 10%, 20%, 30%, 40%, 50%, 60%, 70%, 80%, 90% or greater) relative to number prior to treatment. The number of metastatic nodules may be measured by any reproducible means of measurement. For example, the number of metastatic nodules may be measured by counting metastatic nodules visible to the naked eye or at a specified magnification (e.g., 2×, 10×, or 50×).

Treating cancer can result in an increase in average survival time of a population of subjects treated according to the present invention in comparison to a population of untreated subjects. For example, the average survival time is increased by more than 30 days (more than 60 days, 90 days, or 120 days). An increase in average survival time of a population may be measured by any reproducible means. An increase in average survival time of a population may be measured, for example, by calculating for a population the average length of survival following initiation of treatment with the compound of the invention. An increase in average survival time of a population may also be measured, for example, by calculating for a population the average length of survival following completion of a first round of treatment with a pharmaceutically acceptable salt of the invention.

Treating cancer can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with a pharmaceutically acceptable salt of the invention. A decrease in the mortality rate of a population may also be measured, for example, by calculating for a population the average number of disease-related deaths per unit time following completion of a first round of treatment with a method of the invention.

Compositions

Within the scope of this invention is a composition that contains a suitable excipient and one or more of the pharmaceutically acceptable salts described above. The composition can be a pharmaceutical composition that contains a pharmaceutically acceptable excipient, a dietary composition that contains a dietarily acceptable suitable excipient, or a cosmetic composition that contains a cosmetically acceptable excipient.

The term "pharmaceutical composition" refers to the combination of an active agent with a excipient, inert or active, making the composition especially suitable for diagnostic or therapeutic use in vivo or ex vivo. A "pharmaceutically acceptable excipient," after administered to or upon a subject, does not cause undesirable physiological effects. The excipient in the pharmaceutical composition must be "acceptable" also in the sense that it is compatible with the active ingredient and can be capable of stabilizing it. One or more solubilizing agents can be utilized as pharmaceutical excipients for delivery of an active compound. Examples of a pharmaceutically acceptable excipient include, but are not limited to, biocompatible vehicles, adjuvants, additives, and diluents to achieve a composition usable as a dosage form.

As described above, the pharmaceutical compositions of the present invention additionally include a pharmaceutically acceptable excipient, which, as used herein, includes any and all solvents, diluents, or other liquid vehicle, dispersion or suspension aids, surface active agents, isotonic agents, thickening or emulsifying agents, preservatives, solid binders, and lubricants, as suited to the particular dosage form desired. Remington's Pharmaceutical Sciences, Sixteenth Edition, E. W. Martin (Mack Publishing Co., Easton, Pa., 1980) discloses various excipients used in formulating pharmaceutical compositions and known techniques for the preparation thereof. Except insofar as any conventional excipient medium is incompatible with the compounds of the invention, such as by producing any undesirable biological effect or otherwise interacting in a deleterious manner with any other component(s) of the pharmaceutical composition, its use is contemplated to be within the scope of this invention.

The above-described composition, in any of the forms described above, can be used for treating cancer, or any other disease or condition described herein. An effective amount refers to the amount of an active compound/agent that is required to confer a therapeutic effect on a treated subject. Effective doses will vary, as recognized by those skilled in the art, depending on the types of diseases treated, route of administration, excipient usage, and the possibility of co-usage with other therapeutic treatment.

A pharmaceutical composition of this invention can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent. In addition, fixed oils are conventionally employed as a solvent or suspending medium (e.g., synthetic mono- or diglycerides). Other commonly used surfactants, such as, but not limited to, Tweens or Spans or other similar emulsifying agents or bioavailability enhancers, which are commonly used in the manufacture of pharmaceutically acceptable solid, liquid, or other dosage forms also can be used for the purpose of formulation.

A composition for oral administration can be any orally acceptable dosage form including capsules, tablets, emulsions and aqueous suspensions, dispersions, and solutions. When aqueous suspensions or emulsions are administered orally, the active ingredient can be suspended or dissolved in an oily phase combined with emulsifying or suspending agents. If desired, certain sweetening, flavoring, or coloring agents can be added.

Combination Therapies

In some embodiments, the pharmaceutical composition may further include an additional compound having anti-proliferative activity. It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder, or they may achieve different effects (e.g., control of any adverse effects).

EXAMPLES

Example 1. β-GPA Pharmacokinetics

Method: Subjects were administered RGX-202 (a highly compressible salt form of β-GPA) in a regimen of 600 mg BID, 1,200 mg BID, 2,400 mg BID, or 3,600 mg BID, and plasma samples were taken from the subjects and tested using the protocol described below for levels of β-GPA over the course of 24 hours after administration.

The analyte, β-GPA, and internal standard (IS), [13C415N3]-β-GPA, are extracted from 50.0 µL of human plasma by a protein precipitation extraction procedure. The extraction procedure begins with the addition of 50.0 µL of internal standard working solution to all wells except double blanks, which receive 50.0 µL of water. Next the plate is covered and vortexed. Then 500 µL of acetonitrile/methanol (50/50, v/v) is added to all wells. Next the plate is covered, vortexed and centrifuged. Using a Tomtec Quadra 4, 200 µL of the supernatant is transferred into a new plate. Then 300 µL acetonitrile/methanol (50/50, v/v) is added to all wells. The plate is then sealed and vortexed. The extracts are chromatographed under reverse phase conditions on a Luna HPLC column 50×2.0 mm, 3 µm column using a gradient system with 10 mM ammonium acetate in water and acetonitrile. The compounds are detected and quantified by tandem mass spectrometry in positive ion mode on a MDS Sciex API 4000 equipped with a Turbo Ionspray® interface.

Results: As shown (by dose normalized accumulation ratios) in Table 1 below, administration with 2,400 mg BID or 3,600 mg BID of β-GPA results in higher than expected AUC and $C_{max}$ levels in the subjects.

TABLE 1

| Dose | Average $AUC_{0-24}$ (ng-hr/mL) | Dose-Normalized Average $AUC_{0-24}$ (ng-hr/mL) | AUC Dose Acc. Ratio | Average $C_{max}$ (ng/mL) | Dose Normalized Average $C_{max}$ (ng/mL) | $C_{max}$ Dose Acc. Ratio |
|---|---|---|---|---|---|---|
| 600 mg BID | 15,700 | 13.1 | 1.0 | 1,400 | 1.2 | 1.0 |
| 1,200 mg BID | 45,200 | 18.8 | 1.4 | 4,790 | 2.0 | 1.7 |
| 2,400 mg BID | 164,800 | 34.3 | 2.7 | 26,800 | 5.6 | 4.8 |
| 3,600 mg BID | 241,097 | 33.5 | 2.6 | 47,660 | 6.6 | 5.7 |

Example 2. β-GPA for the Treatment of GI Tumors

Method: Subjects with advanced gastrointestinal tumors (e.g., locally advanced and unresectable, or metastatic) were administered multiple doses of orally administered RGX- 202 as a monotherapy or in combination with irinotecan, folinic acid, and fluorouracil. In the monotherapy arm of the study, RGX-202 was administered orally twice or three times daily on days 1-28 of each 28-day cycle. The dose regimen was dependent on the cohort in which the patient was enrolled. In the combination arm of the study, RGX-202 was administered in the same way as described for the monotherapy arm in combination with FOLFIRI. FOLFIRI was administered by intravenous administration of irinotecan (180 mg/m$^2$) over 90 minutes concurrently with intravenous administration of folinic acid (400 mg/m$^2$) over 2 hours, followed by fluorouracil (5-FU) (400 mg/m$^2$) intravenous bolus and then 5-FU (2400 mg/m$^2$) intravenous infusion over 46 hours, on days 1 and 15 of each 28-day cycle.

During the dose escalation, subjects were evaluated for pharmacokinetics (using the method as described in Example 1), pharmacodynamics, safety, and efficacy of the drug.

Results: The subjects did not exhibit dose limiting toxicity. Objective monotherapy (RGX-202) and combination therapy (RGX-202+FOLFIRI) activities were observed. Of the 7 subjects who received the combination therapy, 6 subjects showed stable disease (as described by RECIST 1.1 guidelines) after 40 weeks of treatment (e.g., doses of RGX-202≥1,800 mg BID). Of the 10 subjects who received the monotherapy, one subject exhibited a partial response (at a dose of 3,600 mg BID after 40 weeks), and three exhibited stable disease (at doses of 1,200 mg BID, 2,400 mg BID, and 3,600 mg BID).

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features herein before set forth. This application claims the benefit of U.S. provisional Ser. No. 62/946,581, filed Dec. 11, 2019, which is incorporated herein in its entirety.

What is claimed is:

1. A method of treating cancer in a subject in need thereof, the method comprising administering between about 2,400 mg and about 3,600 mg of β-guanidinopropionic acid (β-GPA), or a pharmaceutically acceptable salt thereof, to the subject twice per day.

2. The method of claim 1, wherein the method comprises administering about 2,400 mg of β-GPA, or a pharmaceutically acceptable salt thereof to the subject twice per day.

3. The method of claim 1, wherein the method comprises administering about 3,600 mg of β-GPA, or a pharmaceutically acceptable salt thereof to the subject twice per day.

4. The method of claim 1, wherein the method further comprises administering one or more further anti-cancer therapies.

5. The method of claim 4, wherein the one or more anti-cancer therapies comprise radiation therapy, surgery, and/or one or more therapeutic agents.

6. The method of claim 4, wherein the one or more further anti-cancer therapies comprise folinic acid, fluorouracil, irinotecan, and/or oxaliplatin.

7. The method of claim 4, wherein the one or more further anti-cancer therapies comprise folinic acid, fluorouracil, and irinotecan.

8. The method of claim 7, wherein method comprises administering about 180 mg/m$^2$ of irinotecan intravenously over 90 minutes concurrently with about 400 mg/m$^2$ folinic acid intravenously over 120 minutes followed by an about 2400 mg/m$^2$ infusion of fluorouracil intravenously over 46 hours.

9. The method of claim 7, wherein the administering is repeated about every fourteen days.

10. The method of claim 4, wherein the method further comprises surgery.

11. The method of claim 10, wherein the surgery is prior to administration of β-GPA, or a pharmaceutically acceptable salt thereof.

12. The method of claim 1, wherein the cancer is metastatic cancer.

13. The method of claim 1, wherein the cancer is gastrointestinal cancer.

14. The method of claim 13, wherein the gastrointestinal cancer is colorectal cancer, gastric cancer, or adenocarcinoma of the esophagogastric junction.

15. The method of claim 1, wherein the cancer expresses CKB.

16. The method of claim 1, wherein subject is identified to have, or to be at risk of having, metastatic cancer.

17. The method of claim 1, wherein the cancer is resistant to one or more therapeutic agents.

18. The method of claim 1, wherein the cancer progressed on or after treatment with one or more anti-cancer therapies.

19. The method of claim 1, wherein the β-GPA, or a pharmaceutically acceptable salt thereof is the succinate salt of β-GPA.

20. The method of claim 19, wherein the succinate salt of β-GPA is the 2:1 succinate salt of β-GPA.

21. The method of claim 1, wherein the method comprises administering about 2,750 mg to about 3,250 mg of β-GPA, or a pharmaceutically acceptable salt thereof, to the subject twice per day.

* * * * *

UNITED STATES PATENT AND TRADEMARK OFFICE
CERTIFICATE OF CORRECTION

PATENT NO. : 12,011,427 B2
APPLICATION NO. : 17/119661
DATED : June 18, 2024
INVENTOR(S) : Masoud Fakhr Tavazoie et al.

It is certified that error appears in the above-identified patent and that said Letters Patent is hereby corrected as shown below:

In the Claims

Column 10, Claim 9, Line 22, replace "7" with --8--.

Signed and Sealed this
Twenty-sixth Day of August, 2025

Coke Morgan Stewart
*Acting Director of the United States Patent and Trademark Office*